(12) United States Patent
Kahlmeyer et al.

(10) Patent No.: US 7,887,496 B2
(45) Date of Patent: Feb. 15, 2011

(54) JOINT ORTHOSIS

(75) Inventors: Guido Kahlmeyer, Siemerode (DE); Klaus Lidolt, Duderstadt (DE); Helmut Wagner, Duderstadt (DE); Andreas Mühlenberend, Leipzig (DE)

(73) Assignee: Otto Bock Healthcare IP GmbH & Co. KG, Duderstadt (DE)

( * ) Notice: Subject to any disclaimer, the term of this patent is extended or adjusted under 35 U.S.C. 154(b) by 105 days.

(21) Appl. No.: 11/746,627

(22) Filed: May 9, 2007

(65) Prior Publication Data
US 2007/0276305 A1    Nov. 29, 2007

(30) Foreign Application Priority Data
May 9, 2006  (DE) ................ 10 2006 021 789

(51) Int. Cl.
*A61F 5/00* (2006.01)
*E05D 7/00* (2006.01)

(52) U.S. Cl. ................................ 602/16; 16/221

(58) Field of Classification Search .......... 602/1, 602/5, 16, 23, 26; 16/334, 321, 319, 221, 16/368, 369; 49/188, 388, 397
See application file for complete search history.

(56) References Cited

U.S. PATENT DOCUMENTS

| | | | |
|---|---|---|---|
| 1,918,590 A | | 7/1933 | Burton |
| 4,997,438 A | | 3/1991 | Nipper |
| 5,772,618 A | * | 6/1998 | Mason et al. ............... 602/16 |
| 5,807,294 A | * | 9/1998 | Cawley et al. ............. 602/26 |
| 6,413,232 B1 | * | 7/2002 | Townsend et al. .......... 602/16 |
| 2006/0167394 A1 | * | 7/2006 | Ceriani et al. ............. 602/16 |

FOREIGN PATENT DOCUMENTS

| | | |
|---|---|---|
| DE | 19650782 | 10/2007 |
| WO | WO03/017889 | 3/2003 |
| WO | WO2004/024040 | 3/2004 |

OTHER PUBLICATIONS

European Search Report.

* cited by examiner

*Primary Examiner*—Patricia M Bianco
*Assistant Examiner*—Tarla R Patel
(74) *Attorney, Agent, or Firm*—Holland & Hart, LLP

(57) ABSTRACT

A joint orthosis including an upper member, a lower member operably connected to the upper member by one or more swivel axes at a joint mechanism, and a pad attached to the joint mechanism and positioned between the joint mechanism and the body part, wherein the joint mechanism includes a clip connection for securing the pad to the joint mechanism. The upper and lower members include a means for attaching the joint orthosis to a body part of a user, such as an extremity. The clip connection connects to a coupling element that is one or more of an adapter or pad bracket positioned between the joint mechanism and the pad. The pad, pad bracket and/or adapter are configured to cover over the joint mechanism and the pivot axis. The upper and lower members can include teeth that interlock with each other in order to form a synchronized pivot movement.

15 Claims, 6 Drawing Sheets

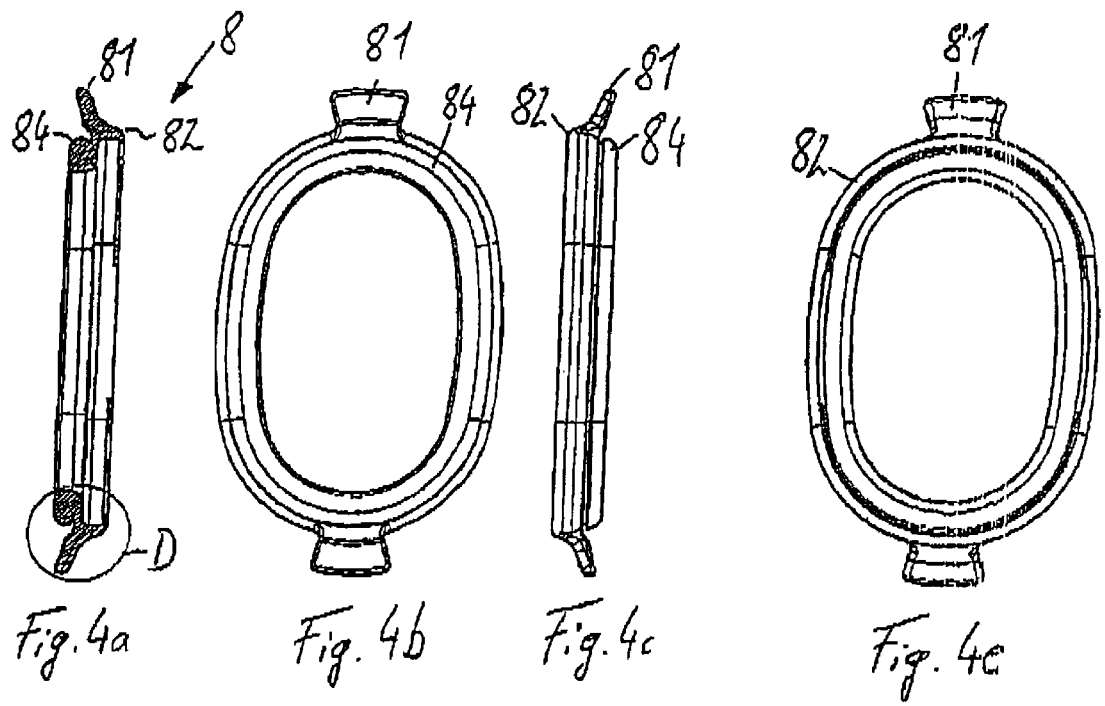

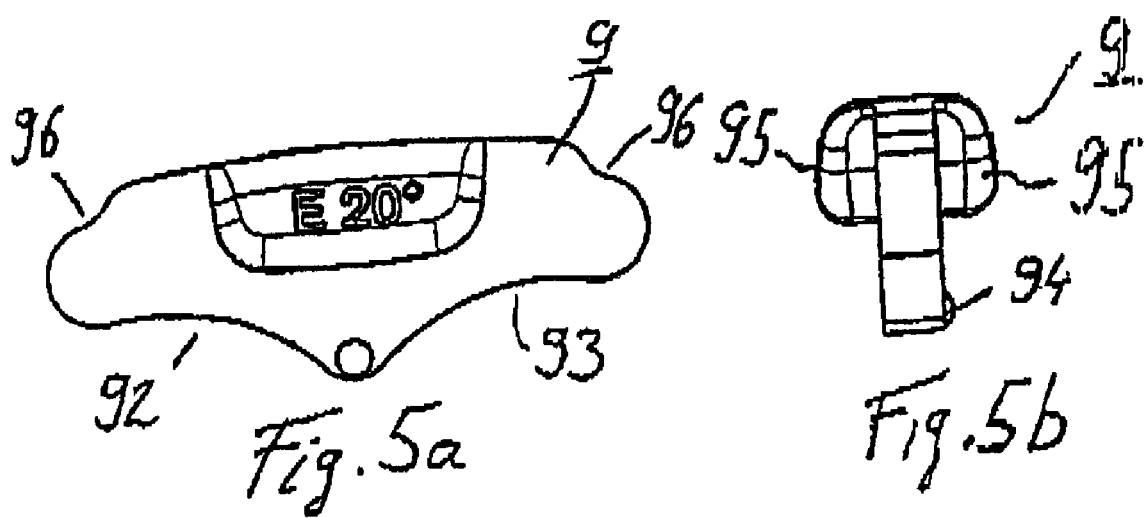

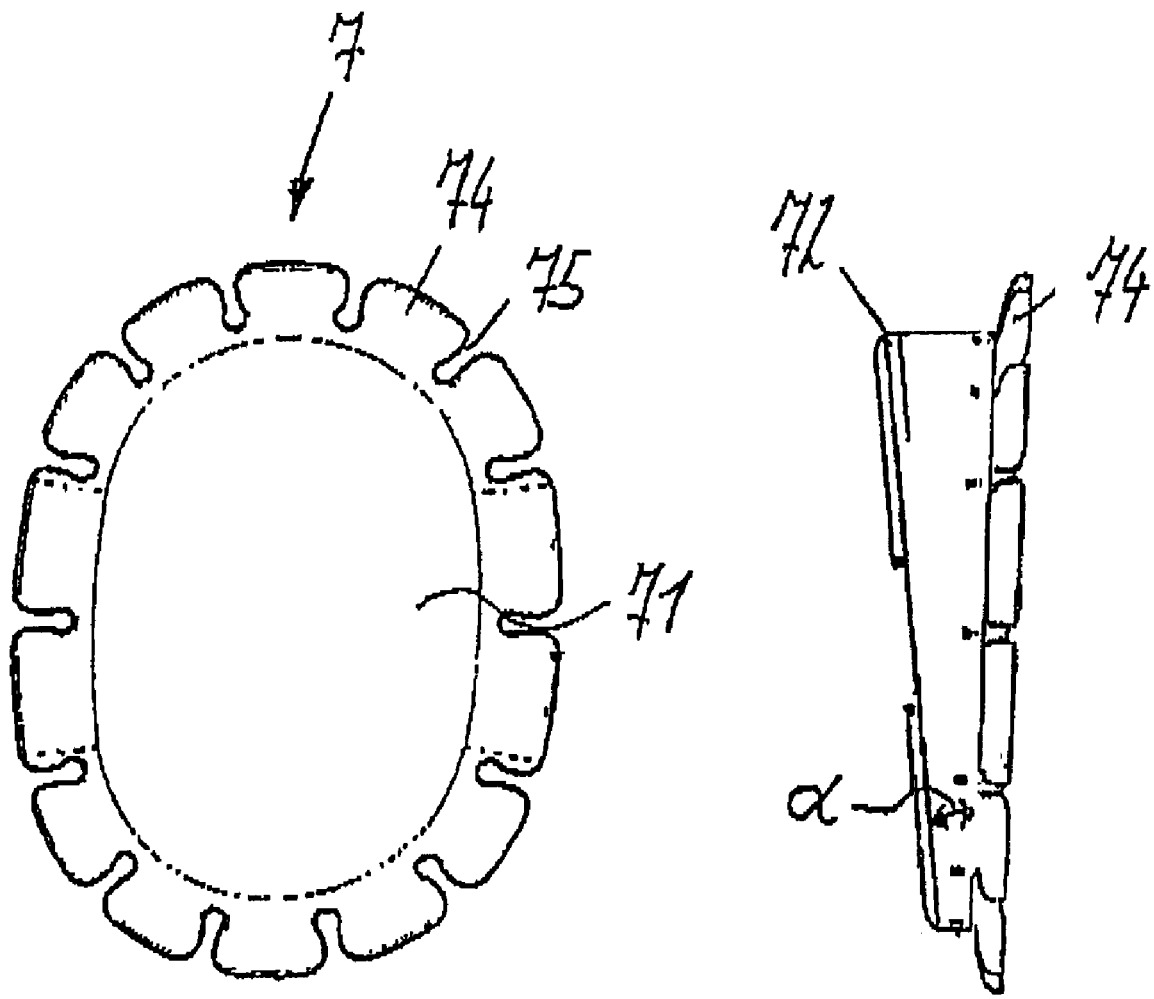

JOINT ORTHOSIS

CROSS REFERENCE TO RELATED APPLICATION

This U.S. patent application claims priority to German Patent Application No. 10 2006 021 789.6, filed on May 9, 2006, entitled "Gelenkorthese" (Joint Orthosis), which is incorporated herein by reference in its entirety for all purposes.

TECHNICAL FIELD

Embodiments of the present invention concern joint orthoses and uses thereof.

BACKGROUND

Joint orthoses are implemented for support and stabilization of joints in the human body. They support physiologically correct movement of the joint, for example after an operation or joint damage. In addition, joint orthoses are used for limitation of the flexion angle in order to enable an adjustment of the maximal angle of flexion for rehabilitation purposes.

Joint orthoses are attached to the body part connected to the joint by a strap, for example, to the upper and lower leg, the lower leg and the foot, the upper arm and the lower arm. The upper and lower parts are equipped with a frame, which consists at least of a splint. A jointed connection of the upper and lower parts or the splints of the upper and lower parts enables pivoting around at least one pivotable axis. In addition to one sided frame parts, two sided frame parts may be located medial and lateral next to the joint to be supported.

In the area of the joint space or joint axis of the joint to be supported, pads are attached which bridge the space between the joint orthosis and the frame of the upper or lower part and create a coupling of the joint orthosis with the body part. The securing of these pads usually occurs via Velcro® type closure or a screw connection. The adjustment and fitting of the individual parameters of the joint to be supported occurs via set screws. To adjust for the various expansion of the extremity or for rehabilitation purposes in the event of swelling joints, exchange of the pad or the pads attached to it is necessary.

SUMMARY

Embodiments of the present invention are directed to a joint orthosis to be worn by a user which allows quick and easy adjustment to a user's physiological features. The joint orthosis includes an upper member, a lower member operably connected to the upper member by one or more swivel axes at a joint mechanism, and a pad attached to the joint mechanism and positioned between the joint mechanism and the body part, wherein the joint mechanism includes a clip connection for securing the pad to the joint mechanism. The upper and lower members include a means for attaching the joint orthosis to a body part of a user, such as an extremity. The clip connection connects to a coupling element that is one or more of an adapter or pad bracket positioned between the joint mechanism and the pad. The pad, pad bracket and/or adapter are configured to cover over the joint mechanim and the pivot axis. The upper and lower members can include teeth that interlock with each other in order to form a synchronized pivot movement

BRIEF DESCRIPTION OF THE DRAWINGS

While the invention is amenable to various modifications and alternative forms, specific embodiments have been shown by way of example in the drawings and are described in detail below. The intention, however, is not to limit any particular embodiments described. On the contrary, embodiments herein are intended to cover all modifications, equivalents, and alternatives falling within the scope of the invention as defined by the appended claims.

FIGS. 4a to 4e represent exemplary schematics of adapters of FIG. 1.

FIGS. 5a and 5b: represent exemplary schematics of stop inserts of FIG. 1.

FIGS. 6a and 6b: represent exemplary schematics of variants of the pad bracket of FIG. 1.

DESCRIPTION OF THE INVENTION

Figure 1:
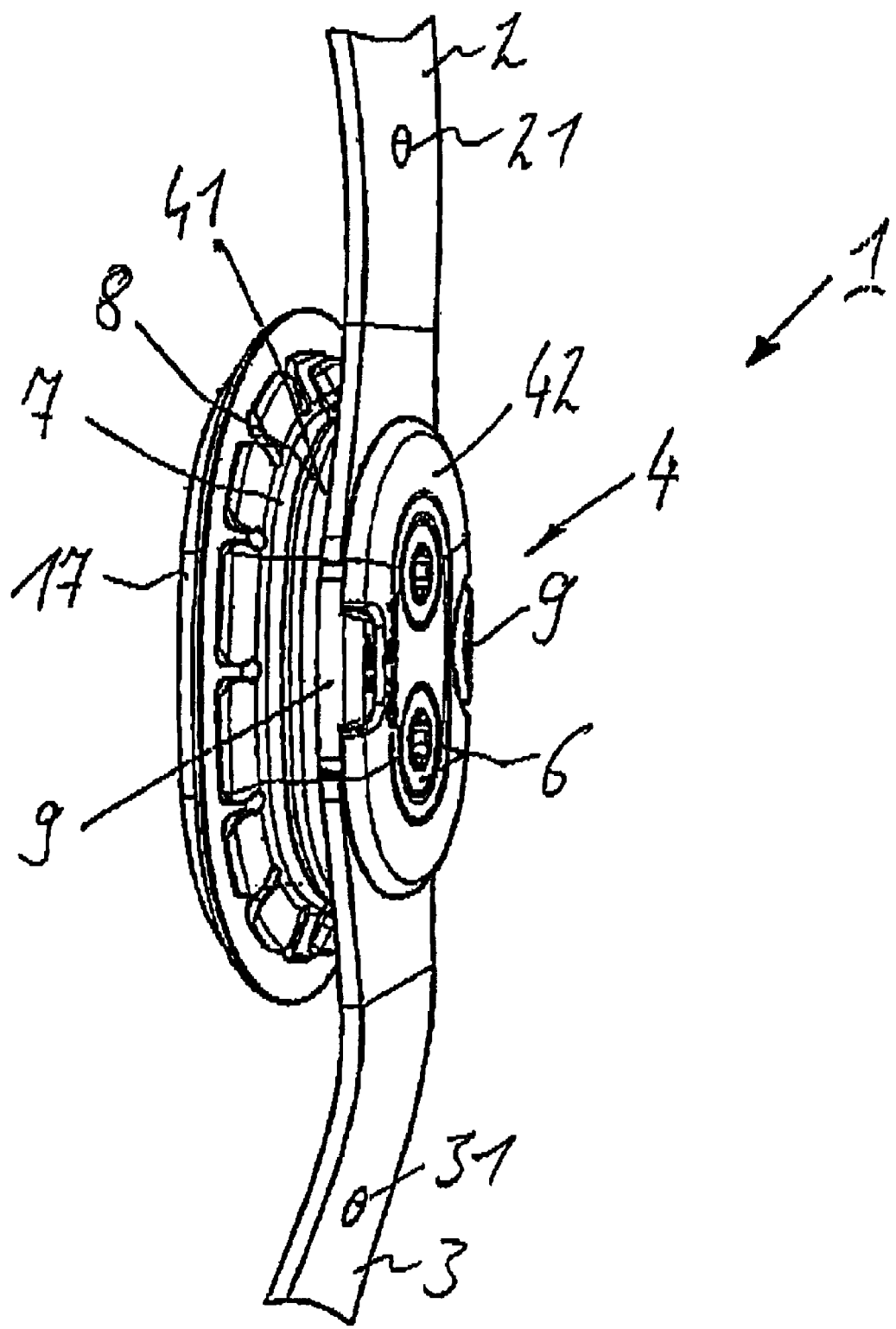
FIG. 1 represents an exemplary schematic of a frame member of a joint orthosis.

In the following sections, various exemplary embodiments are described in order to detail various embodiments of the invention. It will be obvious to one skilled in the art that practicing the various embodiments does not require the employment of all or even some of the specific details outlined herein, but configurations and components may vary.

In one embodiment, the invention relates to a joint orthosis with an upper and lower part connected by at least one pivotable axis, whereby the upper and lower part have equipment for attachment of the joint orthosis to a body part, an extremity in particular, and a pad attached to the orthosis which sits in the interim space between orthosis and body part. This assumes that the joint orthosis, pad or at least one coupling element has key elements which form a clip connection for securing the pad to the joint orthosis. The clipable design, the pad, one of the coupling elements between the pad and the orthosis, and/or the joint mechanism enables adjustment of the pad, in order to provide for various distances between the body part and the joint mechanism for bridging and easy adjustability of the joint orthosis. The pad can be attached immediately to the joint orthosis or joint mechanism or via one or more coupling elements, such as a pad bracket which holds the pad and an adapter ring.

In another embodiment, the invention provides that the pad or a pad bracket is situated on the joint orthosis where there is an under cut on the joint mechanism for attachment of the pad or the coupling element. The coupling element or pad are preferably designed in such a manner that the pivot axis or axes or the joint space which is formed between the upper and lower part, is mostly covered. This can mean that the pad or the coupling element include or surround the pivot axes or joint space between the upper and lower parts. The contact range or holding range of the pad or coupling element is preferably a ring, ring shaped or formed as a bar on which the key elements are provided. Through a relevant cross section formation of the pad or the coupling element, for example by a circumscribed under cut, the overall contact or holding range of the pad or the coupling element can be designed as a key element.

In another embodiment, the invention provides that the upper and lower parts have denticulations or teeth which are preferably included on the frame parts of the upper and lower parts. These denticulations interlock with each other, so that there is a rolling movement of the upper part onto the lower pert. This type of joint mechanism is particularly sensible in knee joint ortheses. For these, the joint mechanism is designed in such a manner that there is a pivot axis on both the upper and lower parts. The pad or coupling element covers the pivot axes and the denticulation area.

In order to avoid exchanging the pad during necessary adjustments, the embodiment provides for the coupling element to function as a pad bracket or adapter, in particular, as an adapter ring which clips between the joint mechanism and the pad, in order to bridge the lateral distance between the pad and the joint mechanism. The adapter or adapter ring and the pad bracket have key elements which correspond to the joint mechanism and the pad, so that by exchange of the adapter or the pad bracket, easy adjustment can be achieved. In addition to the ring shaped design of the adapter, other forms and functions can be realized by the adapter, for example a pivotable position of the pad or the pad bracket.

In another embodiment, the invention provides that the pad or the coupling element, thus the pad bracket or adapter ring, have a wedge shaped cross section in order to be able to realize a diagonally positioned attachment surface of the pad to the extremity or the body part in comparison to the pivot axis.

A symmetrical design for a bilateral situation of joint mechanisms next to the joint to be supported makes the exchange of pads and coupling elements easier, so that the same adapters and pads can be adjusted from a medial and lateral approach. This limits the number of components.

In another embodiment, the invention provides that stops, in particular stop inserts, are positioned on the joint mechanism, in order to set the pivot angle between the upper and lower parts. The stops or stop inserts are attached to the joint mechanism, in particular, clipped on to the mechanism, in order to realize easy exchange. Through this, it is possible to exchange the stops without tools and easily adjust the orthosis in accordance with rehabilitation advancement.

In order to avoid the stops pressing out of the joint mechanism through contact of the upper and lower parts, the pad or the coupling element, in particular the adapter or adapter ring and the pad bracket, are constructed in such a way that the stops are secured. This is achieved by the fact that the pad, adapter and/or pad bracket secure the stops in their clipped-on position and surround them in particular. It is therefore possible that pressing out of the stops is avoided in the flexion direction as well as the extension direction. The stops will also not fall out, which avoids undesired changes to the maximal flexion or extension angle.

In a further embodiment, the design of the invention provides that undercuts are provided on the upper or lower part which block the stops with contact of the upper and lower parts or frame parts. This occurs through a key coupling of the stops with the upper part or the lower part by the undercut grabbing the stop. The stops can also have undercuts, which correspond to the undercuts in the upper or lower part. These are preferably designed in a forcipatory manner, that is, shaped like a forceps.

Various modifications and additions can be made to the embodiments discussed without departing from the scope of the embodiments herein. For example, while the embodiments described above refer to particular features, the scope of can also include embodiments having different combinations of features and embodiments that do not include all of the described features. Accordingly, embodiments herein are intended to embrace all such alternatives, modifications, and variations as fall within the scope of the claims, together with all equivalents thereof.

In FIG. 1, a section of a joint orthosis is represented absent attachment equipment for securing the orthosis to the body part or extremity. Frame part 1 includes an upper section 2 and a lower section 3, which are made of curved splints. Splints 2, 3 are preferably made of light metal that can include, but are not limited to, light-metal alloys, aluminum and aluminum alloys, carbon fiber and carbon steels, copper alloys, magnesium alloys, and titanium and titanium alloys. In bores 21 and 31, attachment media may be inserted for example Velcro® or strap closures as well as padding. Additional metal or synthetic orthosis components may also be attached to the splints 2 and 3. The splints 2 and 3 in this example are attached to each other via a joint mechanism 4.

Figure 2:
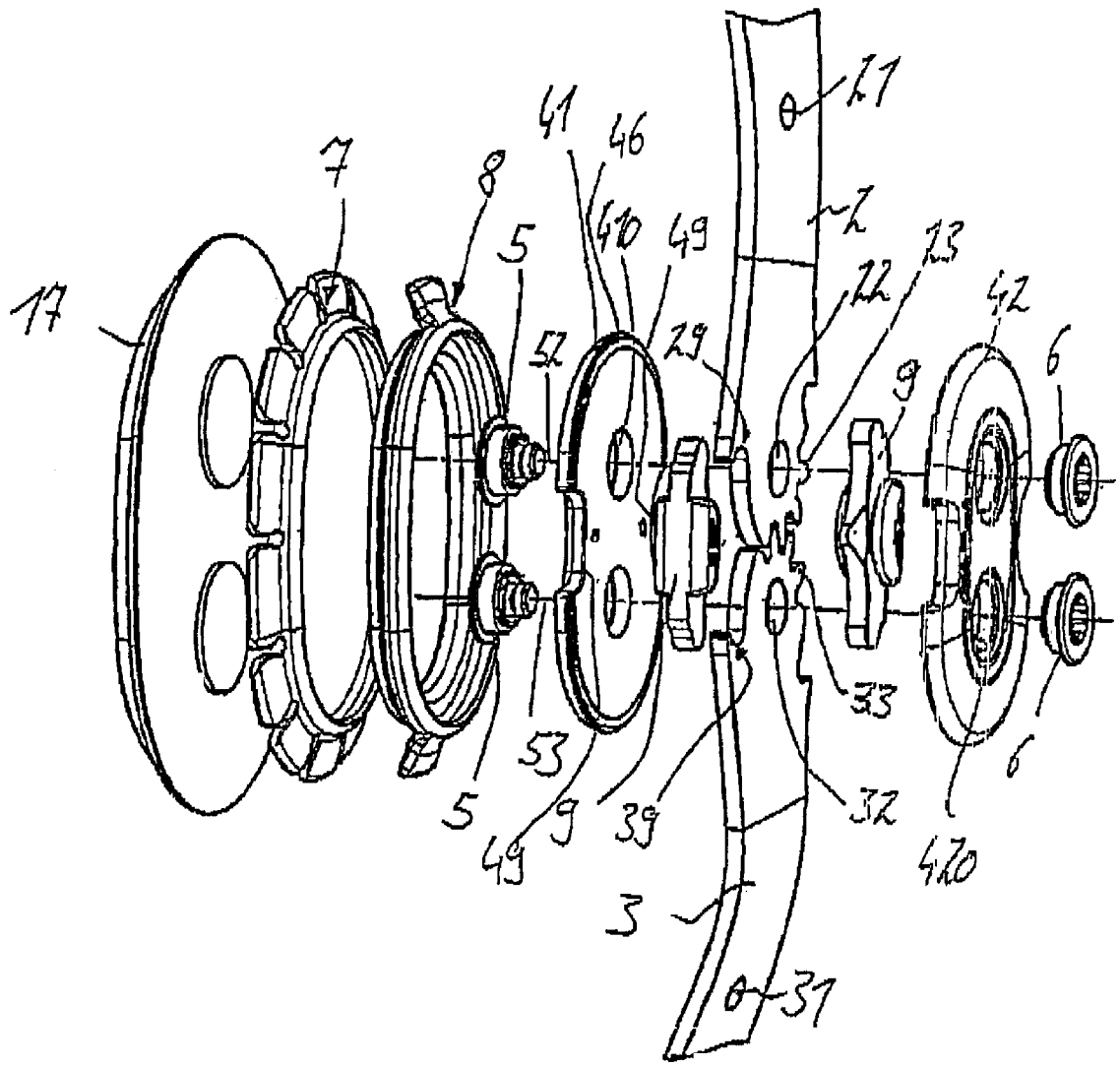
FIG. 2 represents an exemplary exploded view of the frame member of FIG. 1.

The joint mechanism 4, as represented in FIG. 2, includes two discs 41, 42 positioned on either side of splints 2, 3. The discs 41, 42 are attached to each other via fasteners (e.g. screws) 5 and 6, where fastener 5 creates a bolt which is inserted through bores 23, 33 into splints 2, 3. The discs 41, 42 can additionally have through bores 410 and 420, so that two pivot axes 52 and 53 are created for the splints 2, 3. On discs 41 and 42, circumferentially positioned grooves 46, which facilitate attachment of coupling elements in the form of pad brackets 7, adapter rings 8 or pads 17 are formed.

As represented in FIG. 2, splints 2 and 3 have teeth 23 and 33, which are capable of interlocking with each other in order to form a synchronized pivoting movement between upper and lower members. For example, this can be particularly advantageous in knee orthosis, in which splints 2 and 3 are positioned medial to the knee as well as laterally.

Figure 3C:
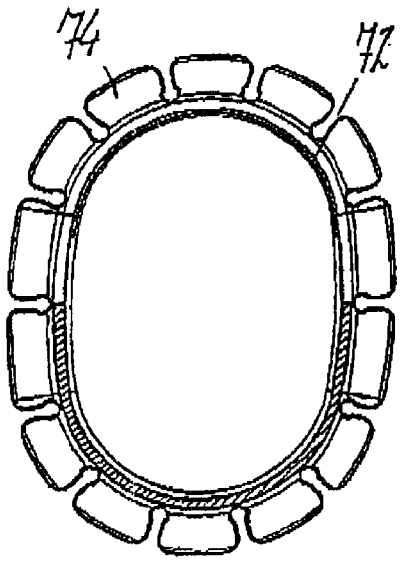
FIGS. 3a to 3e represent exemplary schematics of pad brackets of FIG. 1.
Figure 3A:
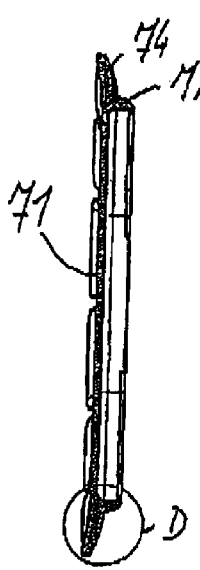
Figure 3B:
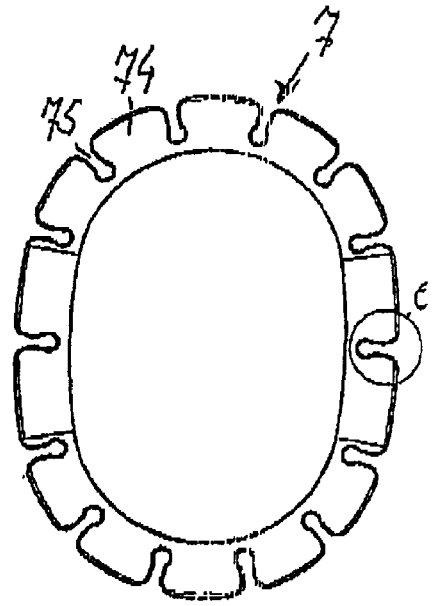
Figure 3E:
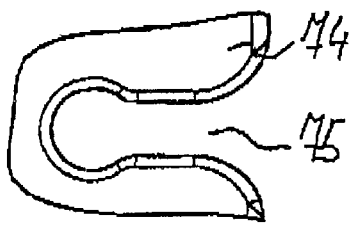
Figure 3D:
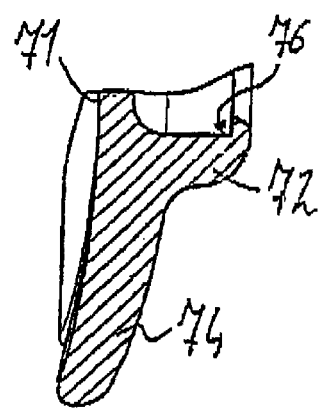

In order to bridge the space between the joint, such as the knee joint, and the joint mechanism 4 in the medial and lateral directions, pads 17 can be used, whose brackets are shown in FIGS. 3a to 3e. FIG. 3a represents a cross section of an exemplary pad bracket, clipped-on between the pad and the joint mechanism 4 as a coupling element, with an attachment side 71 toward the joint and a ring-shaped key element 72, which follows the contour of the joint mechanism 4, primarily an oval. A rear view of this oval is represented in FIG. 3c. The contact surface 71, as represented in the top view of FIG. 3b, is surrounded by an edge 74, which has indentations 75, as shown in FIG. 3e, providing an elastic attachment to the knee joint or to a pad. In the enlarged diagram, FIG. 3d, the key mechanism 76 is represented as cross section which is designed circumferentially. In the key element 72, a groove is shown capable of grabbing into the corresponding key element 46 on the joint mechanism 4 creating a clip connection of the pad bracket and the joint mechanism 4. In order to remove the pad bracket 7 and (e.g. simultaneously) a pad from the joint mechanism 4, the key element lock must be loosened by pulling or bending open and the pad bracket 7; or pad 17 must be removed. In addition to the cross section represented in FIG. 3a, wedge-shaped cross sections are provided on the pad or the pad bracket as represented in FIGS. 6a and 6b to facilitate a diagonal position to the attachment surface 71 relative to the pivot axes or the surface of the joint mechanism 4. In FIG. 6a, the alpha pitch between the attachment surface 71 and the key element 72 or the back side of the pad bracket is demonstrated.

In one embodiment, in order to facilitate lateral or medial adjustability of pad 17, adapter 8 may be inserted between the pad 17 or the pad bracket 7 and the joint mechanism b4, represented in FIG. 4a to 4e. The adapter 8 is in the form of a grooved oval from one side of the key element 82, which represents the key element 72 in the pad bracket 7 or pad 17.

This example enables a clip adapter 8 to attach to the joint mechanism 4. On the other side, an exterior contour 86 is formed, which represents the contour of the joint mechanism 4 with the relevant key element. This contour 84 is represented in the enlarged representation in FIG. 4d. Even here the notch 86 is shown, which is formed corresponding to the notch in the joint mechanism 4. The notch 76 of the pad or the pad bracket 7 can lock into the notch 86 in the adapter 8.

On the distal and proximal ends of adapter 8, tabs 81 are situated, which enable easy removal of adapter 8 from the joint mechanism 4 or an additional adapter 8 through lifting. Multiple adapters 8 can be situated on top of each other in order to bridge larger distances. In addition to a cross section, as seen in FIG. 4a, a wedge-shaped cross section may be formed similar to the formation of the pad bracket 7 in FIG. 6.

As seen in FIG. 2, the teeth 23, 33 can be formed in such a way that a pivot limit occurs in the straight position represented in FIG. 2. This represents a maximum extension of the knee joint. In order to be able to limit flexion of the knee joint, a stop insert 9 may be inserted in to the joint mechanism 4 which is inserted between the discs 41 and 42. The stop insert 9, represented in more detail in FIGS. 5a and 5b, shows depressions 92 and 93, in which the teeth 23 and 33 can freely glide. On at least one side, a key element 94 is represented in the form of an elevation, which locks into the corresponding recess 49 in discs 41 and 42, preventing the stops from falling out. The stop insert 9 can easily be grabbed and pulled out of the joint mechanism 4 via the nub 95, for example, to adjust the flexion angle limits.

Because high pressures may occur beneath the stops in splints 2 and 3 of stop insert 9, forcing the stop insert 9 out of the joint mechanism 4, pad bracket 7 or the adapter 8 are designed such that the stop insert 9 or the nub 95 are at least partially grabbed, so that pressing out is avoided. This design also provides for forcipate, that is, forceps shaped, key elements on splints 2 and 3 capable of locking into the external recesses 96 in the stop inserts 9 and surround the stops, thus fixing them into the joint mechanism 4. Therefore, an exchange of the stops 9 cannot occur even in maximum flexion position.

In one embodiment, the positioning of the stops 9 for limitation of extension and flexion is provided, as seen in FIGS. 1 and 2, but flexion limits can only be set with a set extension angle. For this, the stop inserts 9 may be inserted on one side of the pivot axis 52, 53 at the pivot level.

What is claimed is:

1. A joint orthosis comprising:
   an upper member;
   a lower member operably connected to the upper member by one or more swivel axes at a joint mechanism, the upper member and the lower member including a means of attaching the joint orthosis to a body part of a user and the joint mechanism including a clip connection, and
   a pad member attached to the joint mechanism and positioned between the joint mechanism and the body part, wherein the pad member includes at least one coupling element that connects to the clip connection to secure the pad to the joint mechanism, wherein the pad member is removed from the joint mechanism by pulling or by bending open the connection between the clip connection and the coupling member.

2. The joint orthosis of claim 1, wherein upper and lower members are adapted to be attached to an extremity of a user.

3. The joint orthosis of claim 1, wherein the clip connection comprises a groove disposed on the joint mechanism.

4. The joint orthosis of claim 3, wherein the coupling element is one or more of an adapter or pad bracket positioned between the joint mechanism and the pad.

5. The joint orthosis of claim 4, wherein the adapter, the pad bracket or the pad have a generally wedge shaped cross section.

6. The joint orthosis of claim 1, wherein the upper member and lower members each comprise teeth capable of interlocking at the joint mechanism.

7. The joint orthosis of claim 1, wherein the pad member bracket surrounds the pivot axis and the joint mechanism.

8. The joint orthosis of claim 1, further comprising two joint mechanisms symmetrically positioned opposite one another.

9. The joint orthosis of claim 1, further comprising stop inserts attached to the joint mechanism by attachment elements.

10. The joint orthosis of claim 9, wherein the stop insert is operably coupled to the joint mechanism.

11. The joint orthosis of claim 9, wherein the stop insert is secured by the pad, the pad bracket or the adapter.

12. The joint orthosis of claim 9, wherein the upper and lower members each further comprise a notch configured to engage the stop insert, such that rotation of the upper and lower members about the pivot axis in flexion and extension is blocked upon contact with the stop insert by the notches.

13. The joint orthosis of claim 12, wherein the notches have a forcipate shape.

14. A joint orthosis comprising:
    an upper member;
    a lower member, the upper member and the lower member including structure for attaching the joint orthosis to a body part of a user;
    a joint mechanism connecting the upper member and the lower member along at least one swing axis, the joint mechanism including a groove; and
    a pad member including a coupling element adapted to form a clip connection with the groove to secure the pad member to the joint mechanism, wherein the pad member is removed from the joint mechanism by pulling or by bending open the clip connection.

15. The joint orthosis of claim 14, wherein the coupling element includes a groove corresponding to the groove of the joint mechanism.

* * * * *